(12) United States Patent
Tye

(10) Patent No.: US 6,894,150 B1
(45) Date of Patent: May 17, 2005

(54) NON-PYROGENIC, ENDOTOXIN-FREE, STROMA-FREE TETRAMERIC HEMOGLOBIN

(76) Inventor: Ross Walden Tye, 3 Solar Estates Dr., Chico, CA (US) 95928-6950

( * ) Notice: Subject to any disclaimer, the term of this patent is extended or adjusted under 35 U.S.C. 154(b) by 0 days.

(21) Appl. No.: 09/411,006

(22) Filed: Oct. 1, 1999

(51) Int. Cl.$^7$ ............................ C07K 1/107; C07K 1/14
(52) U.S. Cl. ...................... 530/402; 530/412; 530/418; 530/385
(58) Field of Search .............................. 514/6; 530/385, 530/402, 412, 418

(56) References Cited

U.S. PATENT DOCUMENTS

| | | | |
|---|---|---|---|
| 4,473,494 A | | 9/1984 | Tye .............................. 260/112 |
| 4,529,719 A | * | 7/1985 | Tye .................................. 514/6 |
| 4,650,786 A | | 3/1987 | Wong .............................. 514/6 |
| 4,670,417 A | | 6/1987 | Iwasaki et al. ................. 514/6 |
| 5,028,588 A | | 7/1991 | Hoffman et al. ................ 514/6 |
| 5,084,558 A | * | 1/1992 | Rausch et al. ............... 530/385 |
| 5,189,146 A | | 2/1993 | Hsia ............................ 530/385 |
| 5,234,903 A | | 8/1993 | Nho et al. ....................... 514/6 |
| 5,281,579 A | | 1/1994 | Estep ............................ 514/6 |
| 5,290,919 A | * | 3/1994 | Bucci et al. ................. 530/385 |
| 5,380,824 A | * | 1/1995 | Marschall et al. .......... 530/385 |
| 5,386,014 A | * | 1/1995 | Nho et al. ................... 530/385 |
| 5,532,352 A | | 7/1996 | Pliura et al. ................. 540/145 |
| 5,563,047 A | | 10/1996 | Petersen ..................... 435/68.1 |
| 5,733,869 A | | 3/1998 | Burhop et al. .................. 514/6 |
| 5,750,132 A | | 5/1998 | Gerber ........................ 424/423 |
| 5,753,616 A | | 5/1998 | Rausch et al. .................. 514/6 |
| 5,776,890 A | | 7/1998 | Hoffman et al. ................ 514/6 |
| 5,789,376 A | | 8/1998 | Hsia .............................. 514/6 |
| 5,811,005 A | | 9/1998 | Hsia ........................... 210/483 |
| 5,840,701 A | | 11/1998 | Hsia ............................. 514/21 |
| 5,844,090 A | | 12/1998 | Anderson et al. ........... 530/385 |
| 5,929,031 A | | 7/1999 | Kerwin et al. ................ 514/12 |

OTHER PUBLICATIONS

Cohn, "The Current Status of Haemoglobin–based Blood Substitutes" Ann. Med. 29:371–76 (1997).
Eaton, "Hemoglobin–based blood substitutes: A dream–like trade of blood and guile?" J. Lab. Clin. Med. 127(5):416–7 (1996).
Jones, "Red Blood Cell Substitutes: Current Status" Br. J. Anaesth. 74: 697–703 (1995).
Kroeger et al., "Structures of a Hemoglobin–based Blood Substitute: Insights into the Function of Allosteric Proteins" Structure 5(2):227–37 (1997).
Langermans et al., "Safety evaluation of a polymerized hemoglobin solution in a murine infection model" J. Lab. Clin. Med. 127(5):428–34 (1996).
Lieberthal, "Stroma–free hemoglobin: A potential blood substitute" J. Lab. Clin. Med. 126:231–2 (1995).
Ogden et al., "Haemoglobin–Based Red Cell Substitutes: Current Status" Vox Sang. 69:302–308 (1995).
Winslow, "Blood Substitutes" Science & Medicine 4(2):54–63 (1996).

\* cited by examiner

*Primary Examiner*—Bruce R. Campell
*Assistant Examiner*—Anish Gupta

(57) ABSTRACT

A non-pyrogenic, endotoxin-free, stroma-free, blood substitute capable of being used in humans or other mammals to provide oxygen to tissue and to deliver carbon dioxide to the lung and a process for its preparation are described.

12 Claims, No Drawings

NON-PYROGENIC, ENDOTOXIN-FREE, STROMA-FREE TETRAMERIC HEMOGLOBIN

FIELD OF THE INVENTION

The invention relates to a blood substitute capable of being used in humans or other mammals to provide oxygen to tissue and to deliver carbon dioxide to the lung. More specifically, the invention provides a process for producing a cross-linked tetrameric hemoglobin preparation that is non-pyrogenic, endotoxin-free and stroma-free such that it is capable of in vivo use in a human or other mammals.

BACKGROUND OF THE INVENTION

It is not always practical or safe to transfuse a patient with donated blood. One of the limitations on the use of blood in an emergency setting is the requirement to type and cross-match the blood to minimize the risk of transfusion rejection. Saline cross-matching requires at least 10 minutes and a complete type and cross-match can take up to an hour. Furthermore, the risk of HIV transmission has been estimated to be 1 in 500,000 units of blood and the risk of hepatitis C transmission has been estimated to be 1 in 3,000 units. Schreiber et al., *N. Engl. J. Med.* 334:1685–90 (1996), incorporated by reference in its entirety.

Therefore, a red blood cell ("RBC") substitute has long been sought after. To be effective as a substitute for red blood cells, an RBC substitute ideally will meet several requirements. It must be virus-free, non-toxic and non-immunogenic and it should have satisfactory oxygen carrying capacity and circulatory persistence to permit effective oxygenation of tissues. Preferably, the oxygen affinity should be close to that of whole blood (p50=28 mmHg at 37° C.) (Ogden, J. E. et al., *Vox Sang* 69:302–308 (1995)).

Three general classes of blood substitutes have been investigated: perfluorcarbons, liposome encapsulated hemoglobin and hemoglobin derivatives. Perfluorcarbons are inert chemically synthesized compounds that dissolve oxygen. Perfluorcarbons suffer from the disadvantage that they are immiscible in aqueous solutions and thus must be emulsified with lipids before being introduced into the blood stream. Liposomes suffer from structural rigidity, and from a low effective hemoglobin concentration.

Because hemoglobin mediates the delivery of oxygen from the lungs to the tissues, purified hemoglobin has been extensively investigated as a possible blood substitute. Hemoglobin is reported to be approximately 97% pure inside the red blood cell. Human hemoglobin is a protein having a molecular weight of 64 kD, and it consists of four subunits, two alpha polypeptide chains and two beta polypeptide chains. Each of the subunits contains a single iron-containing heme prosthetic group that binds and releases oxygen. Hemoglobin exhibits cooperative binding of oxygen by the four subunits of the hemoglobin molecule, and this cooperatively facilitates oxygen transport. When hemoglobin binds oxygen, it shifts from the high energy "tense" or "T" state (deoxygenated) to the lower energy "relaxed" or "R" state (oxygenated). Human alpha and beta globin genes have been cloned and sequenced (Liebhaber et al., *Proc. Natl. Acad. Sci. (U.S.A).* 77:7054–58 (1980); Marotta et al., *J. Biol. Chem.* 252:5040–43 (1977); and Lawn et al., *Cell* 21:647 (1980), all of which are incorporated by reference in their entirety).

Because of its natural role in oxygen delivery, hemoglobin has long been the target of efforts to develop a blood substitute. The membranes of red blood cells, which are referred to as ghosts or stroma, contain all of the blood type antigens. Rabiner et al. first demonstrated that some of the toxic properties of hemolyzed red blood cells were related to the membrane (stroma) of red blood cells and their related lipids. Rabiner et al., *J. Exp. Med.* 126:1127 (1967). The membranes are destroyed by freezing so that storage requirements for blood require climate controlled refrigeration. In addition, many of the human viral diseases transmitted through blood transfusions adhere to the stroma of red blood cells. Thus, in view of the immunogenic properties of the cell membranes of red blood cells, and the problems of viral contamination, stroma-free hemoglobin ("SFT") was initially selected for therapeutic research.

An effective stroma-free hemoglobin blood substitute therapy would offer several advantages over conventional blood replacement therapies. Significantly, the use of stroma-free hemoglobin blood substitutes is predicted to reduce the extent and severity of undesired immune responses, and the risk of transmission of viral diseases, including hepatitis and HIV. Moreover, in contrast to the limited storage capacity of erythrocytes, stroma-free hemoglobin blood substitutes are predicted to exhibit an extended shelf life, and to require less rigorous storage facilities.

However, several problems plagued stromal-free hemoglobin isolation procedures. In particular, it was found that the SFH must be free of any part of the red cell membrane as it is the red cell membrane which causes the immune response. Thus complete purification from the stroma was required.

Additionally, once outside of the red blood cell, hemoglobin was found to have such a high affinity for oxygen that it would not release it to the tissues under physiological conditions. SFH was also found to possess only a limited half-life in the body, and to be rapidly cleared from the blood by glomular filtration. This disrupts the ability of the kidney to concentrate urine and results in the rapid removal of hemoglobin from the intravascular volume. Excessive filtration of the alpha/beta subunit by the glomerulus in the kidney can cause osmotic diuresis. In vivo, the retention time of stroma-free human hemoglobin is on the order of 1–4 hours. De Venuto et al., *Transfusion* 17:555 (1977).

The rapid clearing of SFH by the kidney is a consequence of its quaternary molecular arrangement. As indicated above, natural hemoglobin is composed of a tetrameric arrangement of alpha and beta polypeptide chains. Within the RBC, the association of the alpha chain with its corresponding beta chain is very strong and does not disassociate under physiological conditions. The association of one alpha/beta dimer with another alpha/beta dimer, however, is fairly weak and outside of the RBC, the two dimers disassociate even under physiological conditions. Upon disassociation, the dimer is filtered through the glomerulus.

To avoid such removal, SFH has been chemically cross-linked to form a stable tetramer. Several chemical agents have been used to cross-link hemoglobin alpha/beta dimers and prevent their filtration by the glomerulus into the urine, and yet maintain the oxygen transport properties of native hemoglobin. Bis dibromo salicyl fumarate (BDBF) is an activated diester of fumaric acid that has been used as a cross-linker to cross-link hemoglobin (Tye, U.S. Pat. No. 4,529,719, hereby incorporated by reference in its entirety). Fumaric acid is a four carbon straight chain unsaturated trans 2,3 dicarboxylic acid which is capable of interacting with the aspirin binding site of both alpha/beta dimers. This maintains the two dimers in proper orientation for cross-linking with lysine residues. A slight molar excess of BDBF cross-linker to hemoglobin (1.2:1.0), under sub-optimum conditions, has been reported to yield 70% cross-linked hemoglobin molecules.

The tetrameric structure of hemoglobin provides a binding site for 2,3-diphosphoglycerate. Inside red blood cells, the binding of 2,3-diphosphoglycerate to hemoglobin decreases the hemoglobin's oxygen affinity to a level compatible with oxygen transport. The binding of 2,3-diphosphoglycerate to hemoglobin is very weak and requires very high concentrations (i.e., concentrations approaching 1 M or more) in order to modify the affinity of hemoglobin for oxygen. Thus, when the red blood cells are ruptured to produce SFH, the 2,3-diphosphoglycerate is not retained in close proximity to the hemoglobin and disassociates from the hemoglobin. As a consequence, unless further modified, SFH exhibits a higher affinity for oxygen than does hemoglobin in RBCs. The increased affinity of the SFH for oxygen is quite significant since, under physiological conditions, it is unable to release the bound oxygen to the tissues. Bovine hemoglobin does not require 2,3-DPG to maintain a p50 for oxygen in the range of 30 mm.

Cross-linking the alpha or beta chains of hemoglobin will prevent disassociation of the tetramer. It is the disassociation of R state hemoglobin into dimers which allows hemoglobin in the plasma to be filtered by the glomerulus into urine and removed by haptoglobin into the reticuloendothelial system.

The tetrameric structure of T state deoxyhemoglobin has increased stability from six ionic bonds and while in the T state, hemoglobin is effectively prevented from disassociating into dimers. Id this conformation, the beta cleft contact area between the two beta chains (also known as the beta pocket, phosphate pocket, and 2,3-diphosphoglycerate binding site) in deoxyhemoglobin is substantially different than in oxyhemoglobin. The changed conformation of the beta cleft in the T state is believed to explain the decreased oxygen affinity stabilized by 2,3-diphophoglycerate. The T state of hemoglobin is stable and resistant to denaturation. Thus, cross-linking the SFH addresses both the problem of oxygen affinity and the problem of rapid filtration by the kidney.

Other blood substitutes have been described (Tye, U.S. Pat. No. 4,529,719), and may be employed in cases of acute and severe blood loss. However, a need still exists for a blood substitute that exhibits even lower pyrogenicity, and which may therefore be employed in non acute cases or in cases of less severe need, or for chronic, long term or non-emergency transfusion use. The present invention provides such an improved blood substitute.

SUMMARY OF THE INVENTION

This invention is directed to a method for producing a purified preparation of an endotoxin-free, stroma-free, cross-linked tetrameric hemoglobin, and to an endotoxin-free, stroma-free, cross-linked tetrameric hemoglobin.

In detail, the invention provides, a non-pyrogenic, endotoxin-free, oxygen-free, stroma-free, cross-inked tetrameric hemoglobin. The invention particularly concerns the embodiments in which the hemoglobin has been cross-linked with bis dibromo salicyl fumarate and/or has been modified by reaction with pyridoxal-5'-phosphate. The invention particularly concerns the embodiments in which the hemoglobin is human hemoglobin, or is bovine or porcine hemoglobin. Such molecules may be obtained from any of a variety of sources (for example, from animal sources, via recombinant technology, from chemical synthesis, etc.).

The invention also provides a non-pyrogenic, endotoxin-free, oxygen-free, stroma-free, cross-linked tetrameric hemoglobin.

The invention further provides a blood substitute composition comprising a preparation of non-pyrogenic, endotoxin-free, stroma-free, cross-linked tetrameric hemoglobin, and a pharmaceutically acceptable carrier.

The invention further provides a method of supplementing the blood of a mammal which comprises administering to the mammal a blood substitute composition comprising a preparation of non-pyrogenic, endotoxin-free, stroma-free, cross-linked tetrameric hemoglobin and a pharmaceutically acceptable carrier.

The invention further provides a preparation of non-pyrogenic, endotoxin-free, stroma-free, cross-linked tetrameric hemoglobin produced by the process comprising the steps of:

(A) removing endotoxin from a preparation containing red blood cells;

(B) removing oxygen from the preparation containing red blood cells; and (C) lysing red blood cells; or the steps of (A') removing endotoxin from a preparation containing red blood cells;

(B') lysing red blood cells; and (C') removing oxygen from hemoglobin of the lysed red blood cells.

The invention particularly concerns the sub-embodiments wherein in process step (B) or (C'), the oxygen is removed by centrifuging the red blood cells under vacuum.

The invention additionally concerns the sub-embodiment wherein the process for preparing such non-pyrogenic, endotoxin-free, stroma-free, cross-linked tetrameric hemoglobin additionally comprises the steps of:

(D) separating hemoglobin from the stroma of the lysed red blood cells; and (E) cross-linking the separated hemoglobin.

The invention particularly concerns the sub-embodiment wherein process step (A) additionally comprises washing surfaces and equipment that will come into contact with the cross-linked hemoglobin with a dilute solution of hemoglobin.

The invention particularly concerns the sub-embodiments wherein process step (B) or (C') comprises subjecting the red blood cell preparation to a vacuum sufficient to remove oxygen from the preparation. The invention further concerns the sub-embodiment wherein process step (B) additionally comprises centrifuging a solution of the cells under vacuum at a speed sufficient to produce a force greater than the surface tension of the solution.

The invention particularly concerns the embodiment wherein the preparation of endotoxin-free, stroma-free, cross-linked tetrameric hemoglobin additionally contains a pharmaceutically acceptable carrier.

The invention also provides a method for producing a non-pyrogenic, endotoxin-free, stroma-free, cross-linked tetrameric hemoglobin comprising the steps of:

(A) removing endotoxin from a preparation containing red blood cells;

(B) removing oxygen from the preparation containing red blood cells; and (C) lysing red blood cells;

or the steps of (A') removing endotoxin from a preparation containing red blood cells;

(B') lysing red blood cells; and (C') removing oxygen from hemoglobin of the lysed red blood cells.

The invention also concerns the embodiments of such methods wherein in step (B) or (C'), the oxygen is removed by centrifuging the red blood cells under vacuum.

The invention also concerns the embodiment of such method wherein the method additionally comprises the steps of:

(D) separating hemoglobin from the stroma of the lysed red blood cells; and (E) cross-linking the separated hemoglobin.

The invention particularly concerns the sub-embodiment wherein method step (A) additionally comprises washing surfaces and equipment that will come into contact with the cross-linked hemoglobin with a dilute solution of hemoglobin.

The invention particularly concerns the sub-embodiments wherein method step (B) or (C') comprises subjecting the red blood cell preparation to a vacuum sufficient to remove oxygen from the preparation. The invention further concerns the sub-embodiments wherein method step (B) or (C') additionally comprises centrifuging a solution of the cells under vacuum at a speed sufficient to produce a force greater than the surface tension of the solution.

The invention also provides a method of increasing the oxygen carrying capacity of an individual which comprises administering to the individual a non-pyrogenic, endotoxin-free, stroma-free, cross-linked tetrameric hemoglobin. The invention particularly concerns the embodiment wherein the non-pyrogenic, endotoxin-free, stroma-free, cross-linked tetrameric hemoglobin is administered by transfusion or injection.

The invention further concerns the method for increasing an individual's oxygen carrying capacity, wherein the non-pyrogenic, endotoxin-free, stroma-free, cross-linked tetrameric hemoglobin is produced by a process comprising the steps:

(A) removing endotoxin from a preparation containing red blood cells;

(B) removing oxygen from the preparation containing red blood cells; and (C) lysing red blood cells; or the steps of (A') removing endotoxin from a preparation containing red blood cells;

(B') lysing red blood cells; and (C') removing oxygen from hemoglobin of the lysed red blood cells.

The invention particularly concerns the sub-embodiments wherein in process step (B) or (C'), the oxygen is removed by centrifuging the red blood cells under vacuum.

The invention additionally concerns the sub-embodiment wherein the process for preparing such non-pyrogenic, endotoxin-free, stroma-free, cross-linked tetrameric hemoglobin additionally comprises the steps of:

(D) separating hemoglobin from the stroma of the lysed red blood cells; and (E) cross-linking the separated hemoglobin.

The invention particularly concerns the sub-embodiment wherein process step (A) comprises washing surfaces and equipment that will come into contact with the cross-linked hemoglobin with a dilute solution of hemoglobin.

The invention particularly concerns the sub-embodiments wherein process step (B) or (C') comprises subjecting the red blood cell preparation to a vacuum sufficient to remove oxygen from the preparation. The invention further concerns the sub-embodiments wherein process step (B) or (C') additionally comprises centrifuging a solution of the cells under vacuum at a speed sufficient to produce a force greater than the surface tension of the solution.

The invention also provides a container containing a non-pyrogenic, endotoxin-free, stroma-free, cross-linked tetrameric hemoglobin composition. The invention particularly concerns the embodiments in which the container is an anoxic container composed of polyethylene terephthalate, or is an implantable delivery device that delivers a non-pyrogenic, endotoxin-free, stroma-free, cross-linked tetrameric hemoglobin composition to a recipient.

The invention particularly contemplates that the non-pyrogenic, endotoxin-free, stroma-free, cross-linked tetrameric hemoglobin contained in the container is produced through the process comprising the steps of:

(A) removing endotoxin from a preparation containing red blood cells;

(B) removing oxygen from the preparation containing red blood cells;

(C) lysing red blood cells;

(D) separating hemoglobin from the stroma of the lysed red blood cells; and (E) cross-linking the separated hemoglobin; or (A') removing endotoxin from a preparation containing red blood cells;

(B') lysing red blood cells;

(C') removing oxygen from hemoglobin of the lysed red blood cells;

(D') separating hemoglobin from the stroma of the lysed red blood cells, and (E') cross-linking the separated hemoglobin.

The invention particularly concerns the embodiments wherein the hemoglobin of such non-pyrogenic, endotoxin-free, oxygen-free, stroma-free, cross-linked tetrameric hemoglobin has been cross-linked with bis dibromo salicyl fumarate, and/or wherein the hemoglobin has been modified by reaction with pyridoxal-5'-phosphate.

The invention particularly concerns the embodiments wherein the hemoglobin of such non-pyrogenic, endotoxin-free, oxygen-free, stroma-free, cross-linked tetrameric hemoglobin is human, bovine or porcine hemoglobin. Such molecules may be obtained from any of a variety of sources (for example, from animal sources, via recombinant technology, from chemical synthesis, etc.).

DETAILED DESCRIPTION OF THE INVENTION

The present invention concerns a non-pyrogenic, endotoxin-free purified preparation of cross-linked, stroma-free hemoglobin. As used herein, a preparation of hemoglobin is said to be "non-pyrogenic" if it may be administered into an individual of the same species as that from which the hemoglobin was derived (i.e., a human for human-derived hemoglobin, etc.) without causing an immunologic or pyrogenic reaction (such as inflammation, agglutination, clotting, etc.). Any of a variety of assays may be employed to demonstrate the non-pyrogenicity of the compositions of the present invention: interleukin-6 and other cytokine induction (Pool, E. J. et al., *J. Immunoassay* 19:95–111 (1998), Poole, S. et al., *Dev. Biol. Stand.* 69:121–123 (1988)); human monocytoid cell line assays (Eperon, S. et al., *J. Immunol. Meth.* 207:135–145 (1997), Taktak, Y. S. et al., *J. Pharm. Pharmacol.* 43:578–582 (1991)); the Limulus Amoebocyte Lysate (LAL) test (Fujiwara, H. et al., *Yakugaku Zasshi* 110:332–40 (1990), Martel F. et al., *Rev Fr Transfus Immunohematol* 28:237–250 (1985)) and the rabbit pyrogen test (Bleeker W. K. et al., *Prog Clin Biol Res* 189:293–303 (1985), Simon, S. et al., *Dev. Biol. Stand* 34:75–84 (1977); Allison, E. S. et al., *Clin. Sci. Mol. Med.* 45:449–458 (1973)); all herein incorporated by reference. The rabbit pyrogen test is the preferred pyrogenicity assay.

As used herein, a preparation of hemoglobin is said to be "stroma-free" if the hemoglobin has been treated to remove substantially all stromal material, such that the preparation no longer exhibits the immunoreactivity to blood type antigens characteristic of RBCs. Stroma-free hemoglobin thus substantially lacks the toxic and/or pyrogenic properties associated with preparations of hemolyzed red blood cells, and thus can be administered to an individual without causing toxicity or inflammatory reaction. As used herein, a preparation of hemoglobin is said to be "endotoxin-free" if the hemoglobin has been treated to remove substantially all endotoxin. Thus, for the purposes of the present invention, endotoxin-free hemoglobin has an amount of endotoxin ranging from 0–10%, and more preferably from 0–1%, of the amount of endotoxin present in USP water. In a preferred method for forming such endotoxin-free, stroma-free cross-linked hemoglobin, the hemoglobin is deoxygenated to render it "oxygen-free." As used herein, a preparation of hemoglobin is said to be "oxygen-free" if the hemoglobin has been treated to remove substantially all oxygen. Oxygen-free hemoglobin thus is substantially or completely in the higher energy "tense" or "T" configuration.

Although DBDF cross-linked hemoglobin appeared to be very promising based upon it's initial characterization, prior preparations of DBDF cross-linked hemoglobin were found to lack clinical efficacy. The present invention has identified several of properties DBDF cross-linked hemoglobin that have reduced the clinical efficacy of the molecule, and the present invention provides an improved DBDF cross-linked hemoglobin (FXSFH) for overcoming the deficiencies of the prior preparations. Principally, the hemoglobin derivative must be prepared in the absence of oxygen. Inorganic phosphate, which binds tightly to the hemoglobin molecule and interferes with the cross-linking reaction, must be removed to increase yield. Endotoxins, which bind tightly to the hemoglobin molecule and become a hepatic toxin when the hemoglobin is metabolized, must not be allowed to contact the hemoglobin.

Hemoglobin that has been purified from the stroma in the absence of oxygen is referred to as "stroma-free deoxyhemoglobin" ("dSFH") and is in the higher energy "tense" or "T" configuration. Hemoglobin cross-linked in the presence of oxygen binds oxygen very tightly and will not release the oxygen to the tissue under physiological conditions. Removal of oxygen from the hemoglobin solution prior to reaction with DBDF has been very difficult. Concentrated protein solutions froth and foam when oxygen is removed by bubbling nitrogen through the solution or removal of oxygen by placing a vacuum over the solution. One of the problems the art has faced is the lack of an endpoint to discern when all of the oxygen has been removed. When oxygen is removed, there is a change in the pH of the solution which must be compensated for while the reaction occurs. Foaming can be controlled briefly by the addition of a surfactant, but that can introduce additional endotoxins into the final product. Foaming causes denatured protein; surfactant adds endotoxin.

I. Preferred Method for Producing FXSFH

A. Sources of Hemoglobin

The cross-linked stroma-free hemoglobin ("FXSF") of the present invention can be prepared in a single working day with a properly equipped laboratory. Although the chemical reaction itself is extremely rapid, much of the time is spent concentrating hemoglobin, removing reaction products, or equilibrating with physiological buffers.

Stroma-free hemoglobin may be obtained from a variety of mammalian sources, such as, for example, human, bovine, ovine, or porcine sources. Alternatively, the stroma-free hemoglobin of the present invention may be synthetically produced by a bacterial, or more preferably, by a yeast, mammalian cell, or insect cell expression vector system (Hoffman, S. J. et al., U.S. Pat. No. 5,028,588 and Hoffman, et al., WO 90/13645, both herein incorporated by reference. Alternatively, hemoglobin can be obtained from transgenic animals; such animals can be engineered to express non-endogenous hemoglobin (Logan, J. S. et al. PCT Application No. PCT/US92/05000; Townes, T. M. et al., PCT Application No. PCT/US/09624, both herein incorporated by reference).

Preferably, the stroma-free hemoglobin of the present invention is isolated from bovine or human source, and most preferably a human source.

Such hemoglobin, whether derived from an animal, synthetic or recombinant, may be composed of the "naturally existing" hemoglobin protein, or may contain some or be entirely composed of, a mutant hemoglobin protein. Preferred mutant hemoglobin proteins include those whose mutations result in more desirable oxygen binding/release characteristics. Examples of such mutant hemoglobin proteins include those provided by Hoffman, S. L. et al. (U.S. Pat. Nos. 5,028,588 and 5,776,890) and Anderson, D. C. et al. (U.S. Pat. Nos.: 5,844,090 and 5,599,907), all herein incorporated by reference.

B. Cleansing of Membranes and Equipment

Since endotoxins are highly undesirable, it is preferred that all membranes, and equipment used to produce the FXSFH of the present invention be cleansed in a manner sufficient to cause the removal or elimination of endotoxin that may be present on such materials and equipment.

Preferably, such cleansing is accomplished by pre-washing surfaces and equipment that will come into contact with the FXSFH of the present invention using a dilute solution of hemoglobin. Such a solution serves to bind endotoxin and hence to remove residual endotoxin that may be present on such membranes or equipment. The dilute solution of hemoglobin is preferably discarded after each use.

C. Removal of Oxygen

The erythrocyte preparation that is to be used as the source of the hemoglobin of the present invention is treated under conditions sufficient to remove oxygen present in the preparation. One aspect of the present invention concerns an improved process for removing oxygen from SFH preparations. Such deoxygenation may be performed either prior to, or subsequent to erythrocyte membrane disruption.

The removal of contaminating oxygen during the hemoglobin isolation is probably the most critical step in the formation of FXSFH. This step is difficult to accomplish, and most investigators erroneously believe that merely by bubbling nitrogen through the solution for 15–30 minutes they will have removed substantially all of the oxygen present Additionally, investigators do not measure the levels of oxygen in the solution nor do they estimate the amount of "T" state hemoglobin present in their reaction vessels.

The extent of deoxygenation can be measured by gas chromatograph, zirconium-based detector (e.g., a "MOCON" analyzer (Mocon, Minneapolis, Minn.), by measuring $pO_2$ or by measuring the spectral shift that is characteristic of deoxyhemoglobin formation.

1. Removal of Oxygen Prior to Erythrocyte Membrane Disruption A preferred method is to remove the oxygen from the red blood cells that have been washed in isotonic saline prior to hypotonic lysis. The cells still have a large intracellular concentration of 2,3-DPG and thus a lower affinity for oxygen. The cell membrane prevents the hemoglobin protein from foam denaturation.

In this embodiment, oxygen removal is effected by subjecting the erythrocyte preparation to a vacuum sufficient to remove oxygen from the preparation. In a highly preferred embodiment, oxygen removal is accomplished by agitating, or even more preferably, by centrifuging, the cells while under vacuum. Such treatment takes advantage of the fact that oxygen has a looser affinity for hemoglobin contained within cellular membranes than it does for free hemoglobin. By conducting the oxygen removal prior to erythrocyte membrane disruption (i.e., while the hemoglobin is within intact erythrocytes) undesired side effects, such as bubbling or foaming of the protein, and/or its denaturation are avoided or minimized. Centrifugation should be sufficiently extensive to allow deoxygenation, but sufficiently gentle to avoid unacceptable lysis of fragile erythrocytes. Heat may be provided to prevent the solution from freezing. In general, it is preferred to keep the cells at room temperature and to employ a vacuum sufficient to equal the vapor pressure of water at the solution of the temperature. After the removal of oxygen, all further steps are conducted in the absence of oxygen. In a preferred embodiment, such further steps are conducted under nitrogen (or other inert gas) positive pressure in the absence of oxygen.

Emphasis is to be made that while this embodiment provides a significantly improved method for deoxygenating hemoglobin, care must be made to be very thorough in the removal of all traces of oxygen.

Cells that have been treated in the above manner are then lysed by addition of approximately 10 volumes of deoxygenated, endotoxin-free water. The water may be deoxygenated by application of a vacuum and warming of the solution, preferably to its boiling point. The red cell lysis is allowed to proceed and the stroma is subsequently removed by ultrafiltration. After such treatment, the temperatures are equilibrated below room temperature.

All subsequent steps are carried out in the absence of oxygen, maintained by what ever means is desired. A preferred method is the use of a nitrogen positive pressure environmental glove box. Other inert gases (e.g., argon) may be equivalently employed in lieu of nitrogen.

2. Removal of Oxygen Subsequent to Erythrocyte Membrane Disruption

In an alternate preferred embodiment, the erythrocyte membranes are disrupted prior to the deoxygenation procedure. In this embodiment, the SFH has been separated from the stroma prior to deoxygenation, and has also been separated from the high concentration of 2"3' DPG found within red cells. Due to the lowered (or absent) 2"3' DPG concentrations, this SFH will have a relatively high affinity for oxygen. As such, it is subject to foam denaturation during the removal of oxygen.

Accordingly, the erythrocyte preparation is preferably subjected to hypotonic lysis, and the lysate or retentate is then filtered to remove the stroma. Oxygen contaminating the resulting material is removed by vacuum, and more preferably by vacuum centrifugation. The SFH used may be an ultrafiltration obtained from the removal of stroma (dilute) or a retentate from the ultrafiltration of the second stage ultrafiltration conducted to concentrate the hemoglobin to approximately 10% (w/v). Either of these solutions of SFH can be readily deoxygenated by applying a vacuum sufficient to equal the partial pressure of water at the temperature of the solution, while the solution is centrifuged at a speed sufficient to produce a force greater than the surface tension of the solution. These are generally low speeds and can easily be met with preparatory centrifuges, or those of a continuous flow variety. It is desirable to consider the geometry of the containers of the SFH to insure that there will be adequate surface area for gas exchange, and that the temperature can be maintained and the solution not allowed to freeze.

The dSFH prepared in the manner described above is preferably maintained in its inert environment and the pH of the preparation is preferably adjusted to a range between 6.0 and 8.5, and most preferably about pH 7.2. The pH of the solution is preferably adjusted using dilute 0.1 N HCl or 0.1 N NaOH that has been previously determined to be free of endotoxin.

Where dilution, suspension, or addition of water (including buffers, etc.) for other purposes is desired, such water should be deoxygenated and be free of endotoxin. The water may be deoxygenated as described above. All subsequent steps are carried out in the absence of oxygen, maintained by what ever means is desired. As indicated above, a preferred method involves the use of a nitrogen positive pressure environmental glove box., however, other inert gases may be equivalently employed.

D. Membrane Disruption

Hemoglobin may be released from the erythrocyte by hypotonic lysis in twenty volumes of deionized water. Other methods of erythrocyte lysis, such as "slow hypotonic lysis" or "freeze thaw", may also be employed. See, e.g., Chan et al., *J. Cell Physiol.* 85:47–57 (1975), incorporated by reference in its entirety. Under one of the preferred embodiments of the present invention, the cells are lysed by flow mixing deoxygenated red blood cells in isotonic saline with 12 volumes of deoxygenated, deionized, endotoxin-free water and subjecting the cells to gentle agitation.

In order to collect the erythrocytes, the deoxygenated blood samples are washed several times with an isotonic solution and the plasma is separated by centrifugation at 3,000 rpm. Preferably, the isotonic solution used is a saline solution. Preferably, the cells are washed at least three times, rinsed between each centrifugation, and resuspended in a final volume of an equal volume of isotonic solution.

The use of a sonicator is discouraged as it makes membrane spheres (often referred to as "dust"). Agitation methods suitable for use in the present invention include a magnetic stir bar and a mechanical rocker or shaker.

E. Separation Of Stroma From Hemoglobin

The stroma may be removed by ultrafiltration of the oxygen-free hemolysate over a $0.5\mu$ filter which retains the cellular components and passes the hemoglobin. Alternatively, the cellular debris is removed by subsequent filtration through a $0.2\mu$ filter. Ultrafiltration membranes suitable for use in the present invention are commercially available from, for example, Millipore Corporation. This step is preferably performed at 4° C. as rapidly as possible after hemolysis of the erythrocyte, and in an oxygen-free environment. It is understood that other methods of removing the stroma may also be used in the present invention.

F. Removal of Phosphate Ion

Bucci et al. (U.S. Pat. No. 5,290,919) have reported that removal of organic phosphates, e.g., 2,3-diphosphoglycerate, is necessary in human hemolysates because the site of the cross-linking reaction is the same as that occupied by 2,3-diphosphoglycerate in hemoglobin. Accordingly, in a preferred embodiment, the dSFH that has passed through the filter is then treated to exchange phosphate for chloride. For this purpose, the dSFH is passed, in the absence of oxygen, through an ion exchange column that has been previously prepared and equilibrated with chloride. Efficacy of this step is measured by total inorganic phosphate analysis. Suitable ionic resins are commercially available from Pharmacia and Waters. The ionic resin removes phosphate that competes for the aspirin binding site during the reaction with BDBF.

G. Concentration of SFH

After such treatment, the stroma-free hemolysate is concentrated by a membrane that does not allow for the passage of hemoglobin. Preferably, the stroma-free hemolysate is concentrated using a filter having a 30,000 MW cut-off. Preferably, the stroma-free hemolysate is concentrated to a 1%–20% (g/l) solution. More preferably, the stroma-free hemolysate is concentrated to about 5 to about 10%. Most preferably, the stroma-free hemolysate is concentrated to about 10%.

The concentrated solution should be equilibrated with buffer and the pH should be adjusted. Preferably, the pH is adjusted to a pH of 7.40. However, a pH of between about 6.5 and about 8.5 can be used in the present invention.

H. Cross-Linking with BDBF and Reaction with PLP

The completely deoxygenated, phosphate-free SFH is cross-linked to form tetrameric hemoglobin. In a preferred embodiment, the dSFH is cross-linked with bis dibromo salicyl fumarate (BDBF) (Tye, U.S. Pat. No. 4,529,719, hereby incorporated by reference in its entirety). To accomplish this, BDBF cross-linker is added, with stirring to provide mixing, to the dSFH preparation at a molar ratio of BDBF crosslinker dSFH of greater than 1:1. Prior to such addition, the pH of the dSFH preparation is adjusted to match that of the BDBF The pH of the reaction mixture is carefully maintained by the addition of acid or base since the solution is not buffered. This reaction is very quick, taking 5 minutes or less. The reaction is permitted to go to completion (approximately 5 minutes).

Pyridoxal 5 phosphate (PLP) has the ability to modify hemoglobin by introducing a negative charge near a penultimate beta chain histidine residue and by removing a positive charge at the amino terminal end of the same chain. These charge changes stabilize a new molecular configuration that is similar to the hemoglobin-DPG (diphosphoglycerate) complex. Significantly, the hemoglobin of this new configuration has an oxygen affinity resembling that of native hemoglobin within the red cell. The product may have one or two PLP molecules attached per tetramer. Although prior PLP-hemoglobin preparations had a satisfactory oxygen affinity profile, the intravascular retention time was too short to permit such preparations to be acceptable as a resuscitation fluid. Additionally, they were found to cause osmotic diuresis.

Accordingly, after the cross-linking reaction has been completed, pyridoxal 5 phosphate (PLP) is added to the dSFH preparation. The PLP is reduced with sodium borohydride and then permitted to react with the cross-linked dSFH and to form FXSFH-pyridoxal-5'-phosphate (FXSFH-PLP) using the methods described by Benesch et al. (Benesch et al., *Biochemistry* 11:3576 (1972); Benesch et al., *Biochem. Biophys. Res. Commun.* 63(4):1123–9 (1975); Benesch et al., *Methods Enzymol.* 76:147–59 (1981); Benesch et al., *J. Biol. Chem.* 257(3):1320–4 (1982); Schnackerz et al., *J. Biol. Chem.* 258(2):872–5 (1983), all of which references are incorporated by reference in their entirety) with the change that all reagents are free of endotoxin and oxygen and the reaction occurs in the absence of oxygen.

Although the properties of deoxygenated stroma-free human hemoglobin benefit from the above-described pyridoxal 5 phosphate reaction, deoxygenated stroma-free bovine hemoglobin does not require this step.

I. Equilibration

FXSFH can be equilibrated with lactated Ringers solution. After equilibration, the solution is sterile filtered into suitable infusion containers. Infusion containers suitable for use in the present invention include, but are not limited to, sterile IV bags. Preferred infusion containers prevent gas exchange (i.e., impermeable to oxygen) and the FXSFH is stored in the absence of oxygen. This is expected to prevent the heme oxidation to form methemoglobin.

J. Formulations of Blood Substitute Compositions

The FXSFH of the present invention can be formulated into a blood substitute. Such formulations can include other components in addition to the FXSFH. For example, a parenteral therapeutic composition can comprise a sterile isotonic saline solution. The formulations can be either in a form suitable for direct administration, or in a concentrated form requiring dilution prior to administration. The formulations of the present invention can thus contain between 0.001% and 90% (w/v) FXSFH. Suitable compositions can also include 0–200 mM of one or more buffers (for example, acetate, phosphate, citrate, bicarbonate, or Good's buffers). Salts such as sodium chloride, potassium chloride, sodium acetate, calcium chloride, magnesium chloride can also be included in the compositions of the invention at concentrations of 0–2 M. In addition, the compositions of the invention can include 0–2 M of one or more carbohydrates (for example, reducing carbohydrates such as glucose, maltose, lactose or non-reducing carbohydrates such as sucrose, trehalose, raffinose, mannitol, isosucrose or stachyose) and 0–2 M of one or more alcohols or poly alcohols (such as polyethylene glycols, propylene glycols, dextrans, or polyols). The FXSFH of the present invention can also contain 0.005–1% of one or more surfactants and 0–200 mM of one or more chelating agents (for example, ethylenediamine tetraacetic acid (EDTA), ethylene glycol-bis (beta-aminoethyl ether) N,N,N',N'-tetraacetic acid (EGTA), ophenanthroline, diethylamine triamine pentaacetic acid (DTPA also known as pentaacetic acid) and the like). The compositions of the invention can also be at about pH 6.5–9.5.

The FXSFH of the present invention may contains 0–300 mM of one or more salts, for example chloride salts, 0–100 mM of one or more non-reducing sugars, 0–100 mM of one or more buffers, 0.01–0.5% of one or more surfactants, and 0–150 mM of one or more chelating agents. In a still further embodiment, the composition contains 0150 mM NaCl, 0–10 mM sodium phosphate, and 0.01–0.1% surfactant, and 0–50 $\mu$M of one or more chelating agents, pH 6.6–7.8. The formulation may contain 5 mM sodium phosphate, 150 mM NaCl, 0.025% to 0.08% polysorbate 80, and 25 $\mu$M EDTA, pH 6.87.6.

Additional additives to the formulation can include antibacterial agents, oncotic pressure agents (e.g. albumin or polyethylene glycols) and other formulation acceptable salts, sugars and excipients known in the art. Each formulation according to the present invention can additionally comprise constituents including carriers, diluents, fillers, salts, and other materials well-known in the art, the selection of which depends upon the particular purpose to be achieved and the properties of such additives which can be readily determined by one skilled in the art.

The compositions of the present invention can be formulated by any method known in the art. Such formulation methods include, for example, simple mixing, sequential addition, emulsification, diafiltration and the like.

II. Considerations for Production of FXSFH

A. Elimination or Reduction of Endotoxin Contamination

Serum lipases, such as lipase A, do not inactivate endotoxins bound to the hemoglobin molecule. Therefore, endotoxins remain active toxins when taken up by the hepatocyte metabolizing the hemoglobin. Friedman, H. I. et al. reported triad hepatoxicity in a rat model consistent with this theory (See, Friedman, H. I. et al., *Lab Invest* 39:167–77 (1978).

Rausch et al. (U.S. Pat. No. 5,084,558) have reported a substantially endotoxin-free hemoglobin blood substitute. Colpan et al. (U.S. Pat. No. 5,747,663) have reported a process for reducing or removing endotoxins from a cellular lysate solution. Wainwright et al. (U.S. Pat. No. 5,627,266) have described an endotoxin binding protein immobilized to a solid support and the use of this molecule in the removal of endotoxins from solution.

Under one preferred embodiment, the elimination of contamination with endotoxins is ensured by preventing the addition of endotoxins to the chemical processes of the present invention. Typically, endotoxins are added inadvertently by using endotoxin contaminated water. Generally, researchers are more concerned with sterility than endotoxins. Measurement of endotoxins is difficult, and standard LAL binding assays do not work in the presence of hemoglobin. Indeed, because endotoxin binds strongly to hemoglobin, endotoxin levels cannot be accurately measured using the LAL assay in the presence of hemoglobin.

Water is the most likely candidate for introduction of endotoxins because researchers have long recognized that increased number of steps in the preparation of hemoglobin increased the level of toxicity. Preparations using dialysis and filtration methods could easily have exposed the hemoglobin to a thousand volumes of water/buffer contaminated with endotoxin.

The water and the reagents used in the present invention must be substantially free from endotoxin contamination. Preferably, the water and the reagents used in the present invention are completely free from endotoxin contamination. Preparation of FXSFH in the absence of endotoxin is extremely difficult to prepare on the bench top, but in a closed system dedicated to FXSFH manufacture, exclusion of endotoxin would be easier.

One way to reduce the risk of endotoxin contamination is to reduce the amount of water and reagent buffers exposed to the hemoglobin preparation. Therefore, under one preferred embodiment of the present invention, the hemoglobin preparations are made using counter-flow or counter-current dialysis for equilibration of buffers and/or removal of reaction products. Counter flow dialysis methods are suitable for use in the present invention are commercially available (e.g., VariPerm M, bitop, Witten (see, e.g., Schwarz, T. et al, *Electrophoresis* 15:1118–1119 (1994)), Spectrum Laboratories, Inc., Laguna Hills, Calif., etc.). It is estimated that the hollow fiber technique will yield a FXSFH preparation that has a 100 fold reduction in the amount of endotoxin as compared to standard synthesis techniques.

B. Reduction or Elimination of Contaminating Phosphate

Because inorganic phosphate interferes with the cross-linking reaction, it needs to be removed from the hemoglobin in order for the reaction to provide a satisfactory yield. This can be accomplished using a suitable exchange resin with chloride ion. A buffer must be provided if there is a substantial change in the exchange of the phosphate ion for the chloride ion. Preferably, phosphate buffers are not employed during any of the processing steps of the present invention.

Under one embodiment of the present invention, the dSFH solution is substantially free from inorganic phosphate. Preferably, the dSFH solution of the present invention is free from inorganic phosphate. One way of removing inorganic phosphate from the dSFH solution is to pass the SFH solution over an ion exchange matrix equilibrated with chloride. Such a process removes phosphate by competing with phosphate for the aspirin binding site of hemoglobin. This is done in a nitrogen atmosphere. The solution is then concentrated to the desired 10% range and cross-linked using the BDBF cross-linker, at standard atmospheric pressure. If human hemoglobin is used, then the reaction with pyridoxal 5 phosphate and borohydride is carried out under nitrogen in the absence of oxygen.

Preferably, any ion removal or buffer equilibration is performed using counter flow dialysis so as to prevent accumulation of endotoxin in the subsequent product. The material is then sterile filtered into a suitable container.

A second problem has been reported to occur in the preparation of cross-linked hemoglobin for infusion as the phosphate ion must be replaced prior to infusion to prevent binding a buffered species in plasma.

Oxygen affinity of the hemoglobin derivative of the present invention can be measure using the Hemoxyalayser™ (TCS-Medical Products) or the Gill cell described by Dolman et al., *Anal. Biochem.* 87:127 (1978), incorporated by reference in its entirety.

C. Nitrous Oxide Regulation of Arterial Blood Supply

Nitrous oxide is an important regulator of the arterial perfusion of any tissue. Nitrous oxide is synthesized and released by the endothelium in the arterial wall and binds to the hemoglobin in red blood cells. When a tissue is receiving too much oxygen, nitrous oxide is not released and the arterial wall muscle contracts making the vessel diameter smaller, thus decreasing perfusion. When demand for oxygen increases, the desaturated hemoglobin releases nitrous oxide, which causes vasodilatation. The nitrous oxide control of arterial perfusion works over small distances in the arterial supply. Because nitrous oxide binds to hemoglobin inside the red blood cell, it is expected that the nitrous oxide will bind FXSFH as well.

It has been observed that FXSFH infusion causes vasoconstriction of the blood vessels, resulting in extremely high blood pressures in the affected areas. This can make the affected blood vessels very porous, and the FXSFH solution can leak into the surrounding tissues causing the tissues to turn purple. In rabbit models, transfusion of FXSFH through the ear vein has caused cerebral vasculature ischemia and death. Therefore, it is important to minimize the impact of administration of FXSFH on the arterial system during administration.

Under a preferred embodiment of the present invention, nitrous oxide or a vasoactive agent such as verapamil, Atenocard, etc., is administered to the patient prior to FXSFH infusion. This is intended to ensure that the arterial system is minimally changed during infusion. Nitrous oxide and verapamil are preferred vasoactive agents.

Under another preferred embodiment, the infusion rate of the FXSFH solution is slowed down to prevent substantial changes in the arterial system of the patient. Slow channel calcium blockers (or a selective inhibitor of cyclic guanosine monophosphate (cGMP)-specific phosphodiesterase type 5 (PDE5), such as sildenafil citrate) may also be helpful in the prevention of the severe vasoconstriction. However, a slower infusion rate may not be preferred with respect to a trauma patient.

D. Packaging and Storage of FXSFH

The FXSFH of the present invention may be stored in conventional, and preferably oxygen impermeable containers (for example, stainless steel tanks, oxygen impermeable plastic bags, or plastic bags overwrapped with low oxygen permeably plastic bags wherein an oxygen scavenger is placed between the internal plastic bag and the overwrapped plastic bag. In another embodiment, the storage stable hemoglobin solutions can be stored in oxygen permeable or oxygen impermeable ("anoxic") containers in an oxygen controlled environment. Such oxygen controlled environments can include, for example, glove boxes, glove bags, incubators and the like. Preferably the oxygen content of the oxygen controlled environment is low relative to atmospheric oxygen concentrations (see, Kandler, R. L. et al., U.S. Pat. No. 5,352,773; herein incorporated by reference). In a preferred embodiment, the FXSFH of the present invention will be packaged in sealed Tyvek®, or Mylar® (polyethylene terephthalate) bags or pouches. In a second preferred embodiment, the FXSFH of the present invention will be lyophilized and stored as a powder.

The preparations may be stored at room or elevated temperature (Kandler et al., PCT Publication No. WO 92/02239; Nho, PCT Publication No. WO 92/08478, both herein incorporated by reference), or more preferably under refrigeration.

In one embodiment, one or more antioxidants such as ascorbate (Wiesehahn, G. P. et al., U.S. Pat. No. 4,727,027; Kerwin, B. D. et al., U.S. Pat. No. 5,929,031); gluathione, acetylcsyteine, methionine, tocopherol, butyl hydroxy toluene, butyl hydroxy anisole, or pholic compounds. (Österber et al., PCT Publication No. WO 94/26286; Kerwin, B. D. et al., U.S. Pat. No. 5,929,031) may be added to further stabilize the preparation (all such references herein incorporated by reference).

Alternatively, and more preferably, the FXSFH of the present invention will be lyophilized and stored as a powder, or will be packaged in sealed Tyvek®, or Mylar® (polyethylene terephthalate) bags or pouches. Packaging such Kerwin, B. D. et al., U.S. Pat. No. 5,929,031, herein incorporated by reference).

In a preferred embodiment, the FXSFH of such storage containers will be subjected to irradiation or other sterilization treatment sufficient to extend the shelf-life of the compositions.

III. Pharmaceutical Uses of the Compositions of the Present Invention

The FXSFH of the present invention may be used to form pharmaceutical compositions that may be administered to recipients, for example, by infusion, by intravenous or intra-arterial injection, or by other means.

The FXSFH formulations of the present invention can be used in compositions useful as substitutes for red blood cells in any application that red blood cells are used. Such compositions of the present invention formulated as red blood cell substitutes can be used for the treatment of hemorrhage where blood volume is lost and both fluid volume and oxygen carrying capacity must be replaced. Moreover, because the FXSFH of the present invention can be made pharmaceutically acceptable, the formulations of the present invention can be used not only as blood substitutes that deliver oxygen but also as simple volume expanders that provide oncotic pressure due to the presence of the large hemoglobin protein molecule. The FXSFH of the present invention can thus be used as replacement for blood that is removed during surgical procedures where the patient's blood is removed and saved for reinfusion at the end of surgery or during recovery (e.g., acute normovolemic hemodilution or hemoaugmentation, etc.).

A typical dose of the FXSFH of the present invention as a blood substitute is from 10 mg to 5 grams or more of extracellular hemoglobin per kilogram of patient body weight. Thus, a typical dose for a human patient might be from a few grams to over 350 grams. It will be appreciated that the unit content of active ingredients contained in an individual dose of each dosage form need not in itself constitute an effective amount since the necessary effective amount could be reached by administration of a plurality of administrations as injections, etc. The selection of dosage depends upon the dosage form utilized, the condition being treated, the particular purpose to be achieved according to the determination of the ordinarily skilled artisan in the field.

Administration of the FXSFH of the present invention can occur for a period of seconds to hours depending on the purpose of the hemoglobin usage. For example, as a blood delivery vehicle, the usual time course of administration is as rapid as possible. Typical infusion rates for hemoglobin solutions as blood replacements can be from about 100 ml to 3000 ml/hour. However, when used to stimulate hematopoiesis, administration can last only seconds to five minutes and therefore administration rates can be slower because the dosage of the FXSFH of the present invention may be much less than dosages that can be required to treat hemorrhage.

In a further embodiment, the FXSFH of the present invention can be used to treat anemia, by providing additional oxygen carrying capacity in a patient that is suffering from anemia, by stimulating hematopoiesis, and by serving as an adjuvant to erythropoietin therapy. Likewise, the FXSFH of the present invention can be used to provide additional oxygen carrying capacity to an individual (such as an athelete, soldier, mountaineer, aviator, smoke victim, etc.) desiring such additional oxygen carrying capacity. The formulations of the present invention thus are useful in treating hypoxia and ischemia.

In addition, because the distribution in the vasculature of the FXSFH of the present invention is not limited by viscosity or by the size of red blood cells, the compositions of the present invention can be used to deliver oxygen to areas that red blood cells cannot penetrate. These areas can include any tissue areas that are located downstream of obstructions to red blood cell flow, such as areas downstream of thrombi, sickle cell occlusions, arterial occlusions, angioplasty balloons, surgical instrumentation and the like.

In a further embodiment, the FXSFH of the present invention can be used to treat excess nitric oxide concentrations. Excess nitric oxide has been implicated in conditions ranging from hypotension to septic shock. Because the hemoglobin of the present invention can bind nitric oxide and other non-oxygen ligands as well as oxygen, the FXSFH of the present invention can be used to effect the removal excess nitric oxide (or such non-oxygen ligands), or to attenuate the concentration of such nitric oxide and non-oxygen ligands. Such treatment can be accomplished either by administration of FXSFH to the patient, or in an ex vivo manner (as by contacting the patient's blood with immobilized FXSFH, etc.).

The FXSFH of the present invention contains iron, and as such, may be detected via MRI (magnetic resonance imaging). Thus, in a further embodiment, the present invention contemplates the use of FXSFH as an imaging agent.

Although humans have four main red cell antigens (A, B, O and Rh), accounting for 12 main blood types, non-human animals exhibit far greater blood type diversity. The existence of larger numbers of blood types has complicated the use of donated blood in non-human animal transfusions (Hale, A. S., *Vet Clin North Am Small Anim Pract* 25:1323–1332 (1995); Harrell, K. A., et al., *Vet Clin North Am Small Anim Pract* 25:1333–1364 (1995), both references herein incorporated by reference. The FXSFH formulations of the present invention, which can be used regardless of the blood type of the recipient, thus finds additional utility as a blood substitute for non-human animals (e.g., dogs, horses, cats, etc.).

The present invention also concerns implantable delivery devices (such as cartridges, implants, etc.) that contain FXSFH, and that are capable of releasing FXSFH into the circulation in response to a sensed need for increased oxygen carrying capacity. In one embodiment, such devices will deliver FXSFH at a constant rate, so as to facilitate erythropoiesis (either alone, or in combination with erythropoietin). In a second embodiment, the devices will be controlled by sensing means (such as electronic probes of hemoglobin, $O_2$ level, $CO_2$ level, etc.) so as to deliver FXSFH at a rate commensurate with the patient's oxygen carrying capacity needs. Such sensing means may be themselves implantable, or part of the implanted device, or may be located extracorporeally. In a further sub-embodiment, such devices may be used to accomplish or facilitate the hemo-diagnosis of individuals.

IV. Non-Pharmaceutical Uses of the Compositions of the Present Invention

The FXSFH of the present invention may also be used to form non-pharmaceutical compositions that can be used, for example, as reference standards for analytical instrumentation needing such reference standards, reagent solutions, control of gas content of cell cultures, for example by in vitro delivery of oxygen to a cell culture, and removal of oxygen from solutions.

Additionally, the FXSFH of the present invention may be used to oxygenate donated tissues and organs during transport.

In a preferred non-pharmaceutical use, the FXSFH of the present invention may be used to scavenge endotoxin from surfaces or liquids. The invention thus contemplates devices, such as cartridges, filters, beads, columns, tubing, and the like that contain the FXSFH of the present invention. Liquids, such as water, saline, culture medium, albumin solutions, etc., may be treated by passage over or through such devices in order to remove endotoxin that may be present in such liquids, or to lessen the concentration of endotoxin present in such liquids. The FXSFH of such devices is preferably immobilized (as by affinity, ionic, or covalent bonding, etc.) to solid supports present in such devices. In one sub-embodiment, the FXSFH is bound to beads that may be added to the liquids being treated, and then subsequently removed (as by filtration, or affinity immobilization). In a further sub-embodiment, the beads may be of ferromagnetic or paramagnetic metal, or may be themselves magnetic, such that they may be readily separated from the treated liquid by magnetic means.

Likewise, the FXSFH of the present invention may be adsorbed or bound to toweling, air filters, etc. so that endotoxin present on surfaces or in air may be removed or its concentration lessened.

In a similar manner, the FXSFH of the present invention can be used to remove oxygen from solutions requiring the removal of oxygen, and as reference standards for analytical assays and instrumentation.

The FXSFH of the present invention can also be used in vitro to enhance cell growth in cell culture by maintaining oxygen levels.

It will be apparent to those skilled in the art that various modifications may be made in the present invention without departing from the spirit and scope of the present invention. It will be additionally apparent to those skilled in the art that the basic construction of the present invention is intended to cover any variations, uses or adaptations of the invention following, in general, the principle of the invention and including such departures from the present disclosure as come within known or customary practice within the art to which the invention pertains. Therefore, it will be appreciated that the scope of this invention is to be defined by the claims appended hereto, rather than the specific embodiments which have been presented as examples.

What is claimed is:

1. A method for producing a non-pyrogenic, endotoxin-free, stroma-free, cross-linked tetrameric hemoglobin comprising the steps of:

(A) removing endotoxin from a preparation containing red blood cells;

(B) removing oxygen from said preparation containing red blood cells, wherein said oxygen is removed by centrifuging the red blood cells under a vacuum sufficient to remove oxygen from the preparation; and (C) lysing red blood cells.

2. The method for producing a non-pyrogenic, endotoxin-free, stroma-free, cross-linked tetrameric hemoglobin of claim 1, wherein said method additionally comprises the steps of:

(D) separating hemoglobin from the stroma of said lysed red blood cells; and (E) cross-linking said separated hemoglobin.

3. The method of claim 1, wherein said process step (A) additionally comprises washing surfaces and equipment that will come into contact with the cross-linked tetrameric hemoglobin with a dilute solution of a hemoglobin.

4. The method of claim 1, wherein said process step (B) additionally comprises centrifuging a solution of said cells under vacuum at a speed sufficient to produce a force greater than the surface tension of the solution.

5. The method of claim 2, wherein said hemoglobin is human hemoglobin.

6. The method of claim 2, wherein said hemoglobin is bovine or porcine hemoglobin.

7. A method for producing a non-pyrogenic, endotoxin-free, stroma-free, cross-linked tetrameric hemoglobin comprising the steps of:

(A) removing endotoxin from a preparation containing red blood cells;

(B) lysing red blood cells; and (C) removing oxygen from hemoglobin of said lysed red blood cells, wherein said oxygen is removed by centrifuging the red blood cells under a vacuum sufficient to remove oxygen from the preparation.

8. The method for producing a non-pyrogenic, endotoxin-free, stroma-free, cross-linked tetrameric hemoglobin of claim 7, wherein said method additionally comprises the steps of:

(D) separating hemoglobin from the stroma of said lysed red blood cells; and (E) cross-linking said separated hemoglobin.

9. The method of claim 7, wherein said process step (A) comprises washing surfaces and equipment that will come into contact with the cross-linked tetrameric hemoglobin with a dilute solution of a hemoglobin.

10. The method of claim 7, wherein said process step (C) additionally comprises centrifuging a solution of said cells under vacuum at a speed sufficient to produce a force greater than the surface tension of the solution.

11. The method of claim 8, wherein said hemoglobin is human hemoglobin.

12. The method of claim 8, wherein said hemoglobin bovine or porcine hemoglobin.

* * * * *